(12) United States Patent
Golenhofen

(10) Patent No.: US 6,226,347 B1
(45) Date of Patent: May 1, 2001

(54) SIMULTANEOUS X-RAY FLUORESCENCE SPECTROMETER

(75) Inventor: Rainer Golenhofen, Ettlingen (DE)

(73) Assignee: Bruker AXS Analytical X-ray Systems GmbH, Karlsruhe (DE)

( * ) Notice: Subject to any disclaimer, the term of this patent is extended or adjusted under 35 U.S.C. 154(b) by 0 days.

(21) Appl. No.: 09/299,451

(22) Filed: Apr. 26, 1999

(30) Foreign Application Priority Data

May 9, 1998 (DE) .............................. 198 20 861

(51) Int. Cl.[7] .................................. G01N 23/223
(52) U.S. Cl. .................................. 378/45; 378/44
(58) Field of Search .................... 378/45, 35, 44, 378/50, 53, 88, 46, 49, 54

(56) References Cited

U.S. PATENT DOCUMENTS

| 4,140,399 | * | 2/1979 | Janchen ............................. 356/332 |
| 4,564,755 | * | 1/1986 | Winzer et al. ....................... 250/227 |
| 4,639,942 | * | 1/1987 | Puumalainen ........................ 378/45 |
| 4,993,834 | * | 2/1991 | Carlhoff et al. .................... 356/328 |
| 5,461,654 | * | 10/1995 | Grodzins et al. .................... 378/45 |
| 5,497,008 | * | 3/1996 | Kumakhov ........................... 250/505 |

FOREIGN PATENT DOCUMENTS

4407278A1 9/1995 (DE) .
08201320A 8/1996 (JP) .
WO 97/05474 2/1997 (WO) .

OTHER PUBLICATIONS

Manual "Mehrkanal–Rötgenspektrometer MRS 4000" of the company Siemens AG, 1997.

* cited by examiner

*Primary Examiner*—Robert H. Kim
*Assistant Examiner*—Irakli Kiknadze
(74) *Attorney, Agent, or Firm*—Paul Vincent

(57) ABSTRACT

A spectrometer for the simultaneous measurement of several spectral lines from a sample (2) with several wavelength selectors (5a, 6a, 7; 5b, 6b, 7) which supply light of a certain wavelength selectively to a detector (9), wherein each wavelength selector selects a different wavelength, is characterized in that at least two different wavelength selectors (5a, 6a, 7; 5b, 6b, 7) can supply light from the sample (2) to the same detector (9) and that the detector (9) is energy-dispersive and has sufficiently large resolution in order to energy separate the detected light of the various wavelengths from the at least two different wavelength selectors. In this manner it is possible on the one hand to achieve the high resolution of known wavelength-dispersive arrangements with relatively short measuring times due to simultaneous measurements of different wavelength ranges and on the other hand the number of detectors and associated measurement electronics is considerably reduced without requiring in turn a considerably higher effort on the mechanical side of the apparatus.

22 Claims, 3 Drawing Sheets

SIMULTANEOUS X-RAY FLUORESCENCE SPECTROMETER

This application claims Paris Convention priority of German patent application number 198 20 861.8 filed May 9, 1998, the complete disclosure of which is hereby incorporated by reference.

BACKGROUND OF THE INVENTION

The invention relates to a spectrometer for the simultaneous measurement of several spectral lines of a sample with several wavelength selectors each selectively supplying light of a certain wavelength to a detector, wherein usually each wavelength selector selects a different wavelength.

A multiple channel spectrometer of this type is e.g. supplied by the company Bruker AXS GmbH (see manual "Mehrkanal-Röntgenstpektrometer MRS 4000" dated 1997).

In order to examine the optical characteristics of samples, in particular for determining the chemical composition on the basis of specific, optical characteristics of the different atoms and molecules, a multitude of most different spectrometers is used which operate in wavelength ranges from the far-infrared via the visible range to the range of X-rays. In all these spectrometers the sample to be examined is irradiated with light of one or several wavelengths and the light modified by the sample, being characteristic of the sample, is detected either in transmission or reflection and is evaluated in the form of a spectrum.

To obtain spectral resolution of the detected measuring signals, up to now two alternative methods have been used, i.e. the use of an energy-dispersive or a wavelength-dispersive arrangement.

An energy-dispersive spectrometer usually comprises only one single detector which directly receives the radiation to be examined from the sample. Since the detector "faces the sample directly" it does not only receive the interesting "useful radiation" but also the entire background and interfering radiation. In particular, often the detector will be highly influenced by the radiation of the main elements which sometimes are of no interest whatsoever since they are known anyway. In this manner, the signals of the actually interesting elements disappear inside the strong background or interference signals. As a consequence, an energy-dispersive spectrometer of this type has only low resolution and a high detection limit and therefore a relatively low overall performance.

As an alternative, wavelength-dispersive spectrometers are used, like e.g. the initially cited multiple channel X-ray spectrometer "MRS 4000". These devices comprise a multitude of analyzers and detectors, wherein each element to be measured has its own analyzer crystal and its own detector. In this manner, it is possible to receive the signals of various wavelengths simultaneously. The wavelength-dispersive spectrometers are thus very powerful and have a high resolution.

However, the big effort required owing to the many detectors and associated measuring electronics for each wavelength range and the increased vulnerability to disturbances due to the multitude of highly sensitive components is a disadvantage. In particular, the required large number of detectors and independent measuring electronics associated therewith render such spectrometers quite expensive.

WO 97/05474 on the other hand discloses a wavelength-dispersive X-ray fluorescence spectrometer which provides for several analyzers operating in different wavelength ranges with only one single detector. However, this spectrometer does not allow simultaneous measurements of light from all analyzers, but can receive the light from only one single analyzer at a time. By means of corresponding mechanics, the various monochromators consisting each of a focussing analyzer crystal with entrance and exit gap, are successively brought between the sample and the detector and thus the individual parts of the spectrum are recorded successively.

This arrangement has the disadvantage that on the one hand only one single spectral line can be measured at a time. Therefore the spectrometer works extremely slowly compared to other known wavelength-dispersive arrangements like e.g. the above-mentioned "MRS 4000". Although the same detector is used for a variety of different wavelength ranges, its energy dispersion which is of course usually present is not utilized. Furthermore, owing to its moveable parts the device according to WO 97/05474 has the disadvantage of a high mechanical effort, and during operation the complicated mechanics will frequently lead to operational faults.

In contrast thereto, it is the object of the present invention to present a spectrometer for the simultaneous measurement of several spectral lines with the initially described features and which on the one hand achieves the high resolution of known wavelength-dispersive arrangements in combination with relatively short measuring times by simultaneous measurements of different wavelength ranges but which on the other hand considerably reduces the complexity of the apparatus, in particular the number of detectors and associated measuring electronics without having to increase the constructional effort with respect to the mechanical apparatus to a considerable extent.

SUMMARY OF THE INVENTION

According to the invention, this object is achieved in a manner which is at the same time surprisingly simple and effective, in that at least two different wavelength selectors can supply light from the sample to the same detector and that the detector is energy-dispersive and has a sufficiently large resolution in order to separate the energies of the detected light quanta of different wavelengths coming from the at least two different wavelength selectors.

The inventive spectrometer selects at first only the characteristic radiation of the elements to be analyzed from the total radiation emitted by the sample via individual wavelength selectors, just like a conventional wavelength-dispersive spectrometer. Subsequently however, several characteristic lines are simultaneously processed by one single detector in an energy-dispersive manner, whereby the number of detectors can be reduced by at least a factor of 2, in certain embodiments by an even higher factor, in comparison to a conventional wavelength-dispersive spectrometer working simultaneously. In contrast to a purely energy-dispersive spectrometer, in the inventive spectrometer hardly any background radiation reaches the detector and the detector is not overloaded by a main component of the radiation from the sample, which considerably improves the numerical statistics for the remaining interesting elements. In principle, the invention combines the positive characteristics of a wavelength-dispersive simultaneous spectrometer by combining several wavelength-dispersively separated lines on one single detector with the advantages of a conventional energy-dispersive arrangement without having to accept their disadvantages.

In a particularly preferred embodiment, the inventive spectrometer is an X-ray fluorescence spectrometer, wherein the light detected by the sample is X-ray fluorescence light. The spectrometer according to the present invention was developed especially for this application. However, the above-mentioned basic idea of combining the positive characteristics of an energy-dispersive spectrometer and a wavelength-dispersive arrangement can be transferred also to other wavelength ranges.

In case relatively inexpensive detectors with limited energy resolution are used, it is advantageous to provide several detectors each receiving light from the sample only via a few, in the most simple case via only two different wavelength selectors. Even with a relatively low energy resolution of the detector, it will always be possible to select two suitable characteristic lines (or narrow wavelength ranges) out of the interesting ones, which have are sufficiently separated from one another to permit safe separation even using a detector with low energy resolution.

In an extreme case, all interesting characteristic lines can be processed by only one single detector with correspondingly high resolution. In this case the detector should have an energy resolution of $\Delta E < 200$ eV, preferably $\Delta E < 30$ eV at $E = 5.9$ keV.

In an advantageous manner, the components of the inventive spectrometer are selected such that the resolution of the wavelength selectors is higher than the resolution of the associated detector. In this way, relatively narrow wavelength ranges inside a broad energy resolution range of a relatively inexpensive detector can be defined that they are detected by the detector simultaneously and separately.

In a particularly cost-saving embodiment of the inventive spectrometer, the different wavelength selectors are arranged between the sample and the detector essentially in a plane in the form of a star about an axis. This spatial arrangement utilizes the available space to an optimum extent and this embodiment of the spectrometer can be constructed in a particularly compact manner.

In a preferred embodiment of the inventive spectrometer a wavelength selector comprises focussing optics with an entrance slit, an analyzer element and an exit slit.

In further variants of this embodiment, the analyzer elements may be conventional single crystals.

As an alternative, in other further variants, the analyzer elements may also be multilayer structures.

The analyzer elements will preferably comprise a concave curvature and thus have focussing characteristics with respect to imaging the entrance slit onto the exit slit.

In embodiments of particularly simple construction, several wavelength selectors associated with the same detector comprise a common exit slit. The entrance slit, however, will usually be different for each wavelength selector.

In a particularly advantageous variant, at least one wavelength selector comprises an absorbing element. In this manner, it is possible with maximum sample excitation by the X-ray tube to reduce the intensity of particularly strong lines such that also the numerical statistics for much weaker lines which are simultaneously measured on the same detector, remain sufficiently good.

For this reason, in a further improvement of this embodiment, the absorbing elements will be arranged such that all intensities of the light transmitted via all wavelength selectors associated with the same detector differ at the most by one order of magnitude. In this manner, the dynamic range of the detector will not be overstressed and weaker lines are emphasized in relation to stronger lines which helps to considerably improve the numerical statistics of the weaker lines.

Inexpensive embodiments of the inventive spectrometer which do not require too much equipment, comprise between 4 and 10 wavelength selectors. Embodiments are also feasible with considerably more wavelength selectors, e.g. up to 28, like the above-mentioned prior art device "MRS 4000" which requires, however, the same amount of detectors, whereas the inventive spectrometer necessitates considerably less detectors and associated measuring electronics.

In normal embodiments of the inventive spectrometer it will make sense to associate between 2 and 8 wavelength selectors with each detector. In particular, in order to be able to use also very simple and inexpensive detectors, like e.g. proportional counters or scintillation counters, the number of associated wavelength selectors has to be relatively low. In the most simple case of merely two wavelength selectors per detector, the two energies can be easily separated also with low energy resolution of the detector if the two wavelength selectors transmit light at the one and at the other energy band of the detector.

One embodiment of the inventive spectrometer is of particular advantage in which semi-conducting detectors are used as detectors. Since they possess a relatively high energy resolution, considerably more wavelength selectors may be associated with each detector.

Further advantages of the invention can be gathered from the description and the drawing. The features mentioned above and below may be utilized according to the invention individually or in any arbitrary combination with one another. The embodiments shown and described are not to be understood as exhaustive enumeration but rather have exemplary character for describing the invention.

BRIEF DESCRIPTION OF THE DRAWINGS

The invention is shown in the drawing and is further explained by means of embodiments. In the drawing:

FIG. 3b eight wavelength selectors are associated with one detector.

DETAILED DESCRIPTION OF THE PREFERRED EMBODIMENTS

Figure 1:
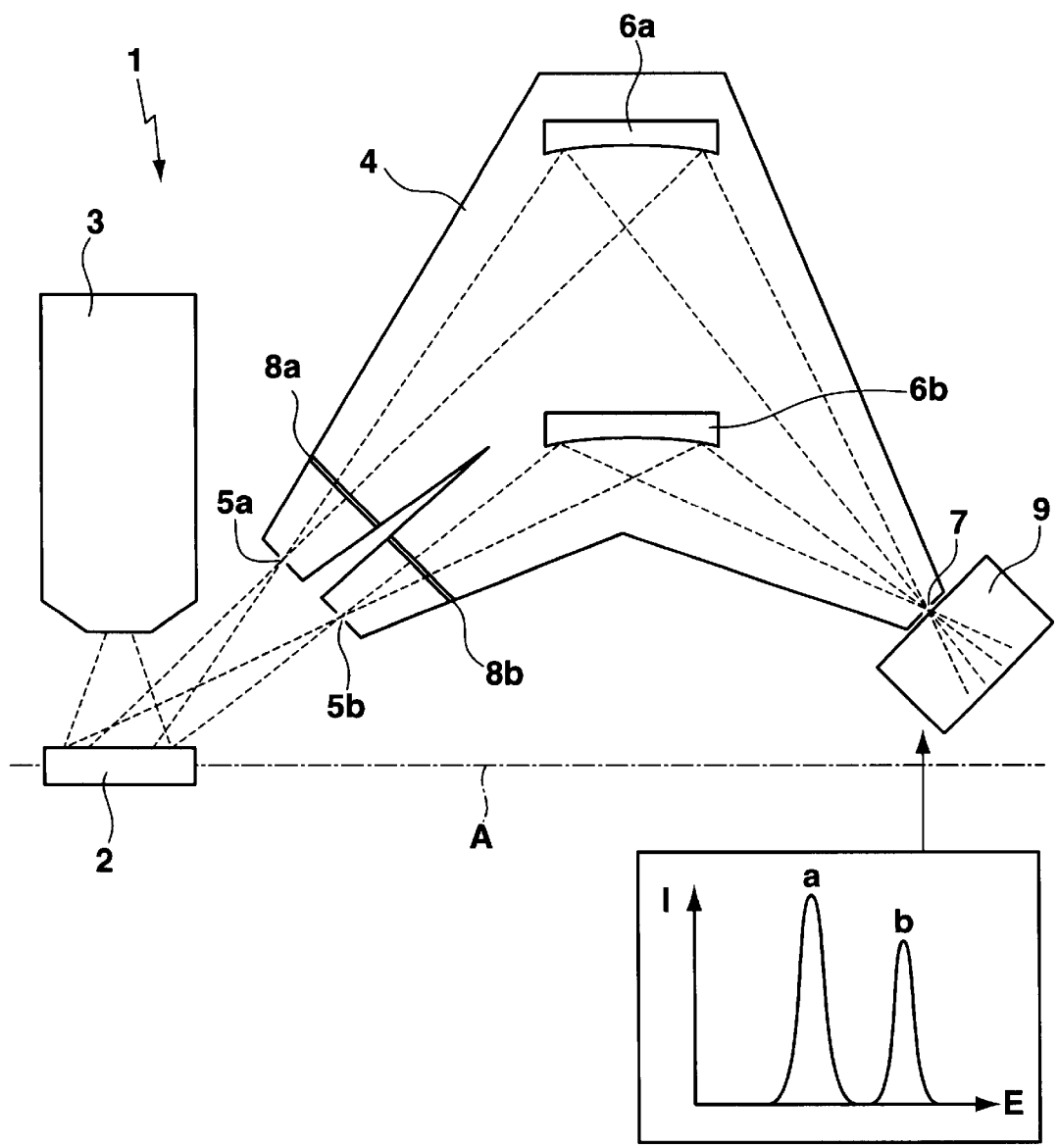
FIG. 1 shows an embodiment of the inventive spectrometer in the form of an X-ray fluorescence spectrometer comprising two wavelength selectors associated with the same detector.

FIG. 1 shows a schematic horizontal cross section of an inventive X-ray fluorescence spectrometer 1 for the simultaneous measurement of several spectral lines from a sample 2. X-ray light is irradiated from an X-ray tube 3 onto the sample 2 which may be solid or liquid. In this embodiment of the invention, in a double monochromator 4 X-ray fluorescence light emitted by the sample 2 is supplied along two different paths to two different wavelength selectors each guiding light of a certain narrow wavelength band that usually differs from selector to selector, to the same detector 9 thus receiving an energy spectrum of X-ray fluorescence light via the two paths a and b schematically shown in the lower right-hand box.

The wavelength selectors of the double monochromator 4 each comprise focussing optics with an entrance slit 5a, 5b, an analyzer element 6a, 6b and a common exit slit 7. Furthermore, the two wavelength selectors of the double monochromator 4 comprise absorbing elements 8a, 8b arranged such that the intensities of the transmitted light of the two wavelength selectors differ at the most by one order of magnitude in order not to overstress the dynamics of the detector 9.

The analyzer elements 6a, 6b may be formed as single crystals or multilayer structures. In the embodiment shown, they each comprise a concave curvature in order to reproduce the X-ray fluorescence light accumulated in the entrance slits 5a, 5b on the common exit slit 7.

Figure 2:
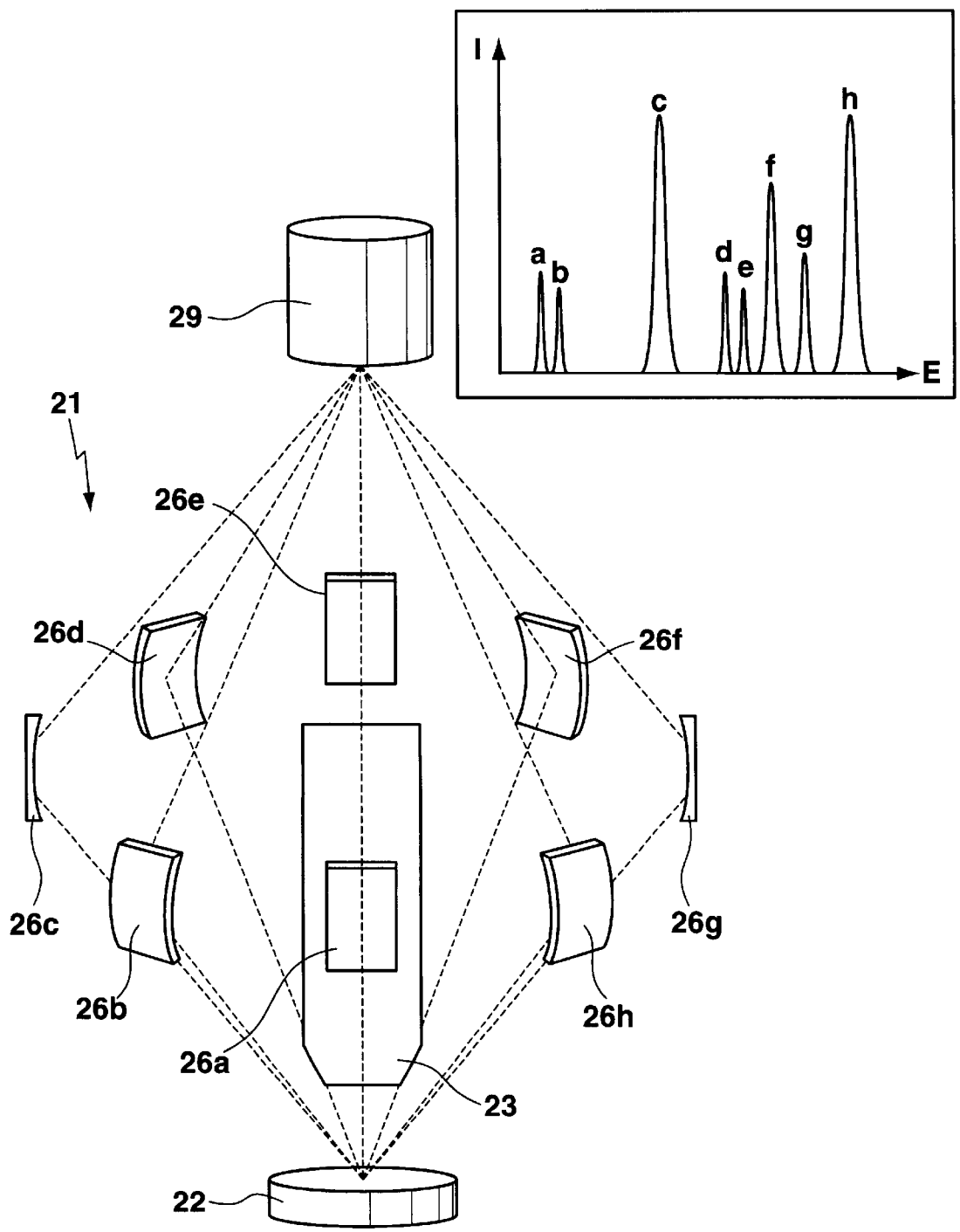
FIG. 2 shows an explosive view of an embodiment comprising eight wavelength selectors.

In other embodiments it is possible to associate considerably more wavelength selectors with the same detector instead of only two wavelength selectors like in FIG. 1. FIG. 2 shows an embodiment of an X-ray fluorescence spectrometer 21 in which X-ray light of an X-ray tube 23 is emitted from a sample 22 in the form of X-ray fluorescence light and supplied to the same detector 29 along eight different wavelength dependent paths via eight different wavelength selectors, represented in the drawing only by the associated analyzer elements 26a to 26h. The different wavelength selectors are arranged between the sample 22 and the detector 29 about an axis in one plane in the form of a star. An example of a spectrum of the light along paths a to h, recorded by detector 29, is shown in the diagram in the box at the top right-hand side of FIG. 2.

One can see the characteristic lines of eight elements contained in sample 22 their signals being simultaneously supplied to detector 29 via the eight different wavelength detectors.

In an extreme case, all characteristic lines can be processed by only one single detector with a corresponding high resolution as in the example of FIG. 2. However, it is also possible to separate merely two characteristic lines, as shown in FIG. 1, by means of a detector which may then exhibit a correspondingly lower resolution.

FIG. 1 shows merely one double monochromator 4 with an associated detector 9. It is, however, possible to arrange in an inventive X-ray fluorescence spectrometer 1 several of said double monochromators 4 with their associated detector 9 in a manner rotationally symmetric about an axis A extending through the sample 2. It is possible to arrange the elements to be analyzed in such a manner that the two energies from the two wavelength selectors are separated by means of very simple detectors, like e.g. proportional counters or scintillation counters.

The detectors 9, 29 may also be semiconductor detectors.

It is essential for the invention, that the detectors 9, 29 are energy-dispersive and have a sufficiently large resolution in order to separate in terms of energy the detected light of the various wavelengths from the different wavelength selectors.

Figure 3A:
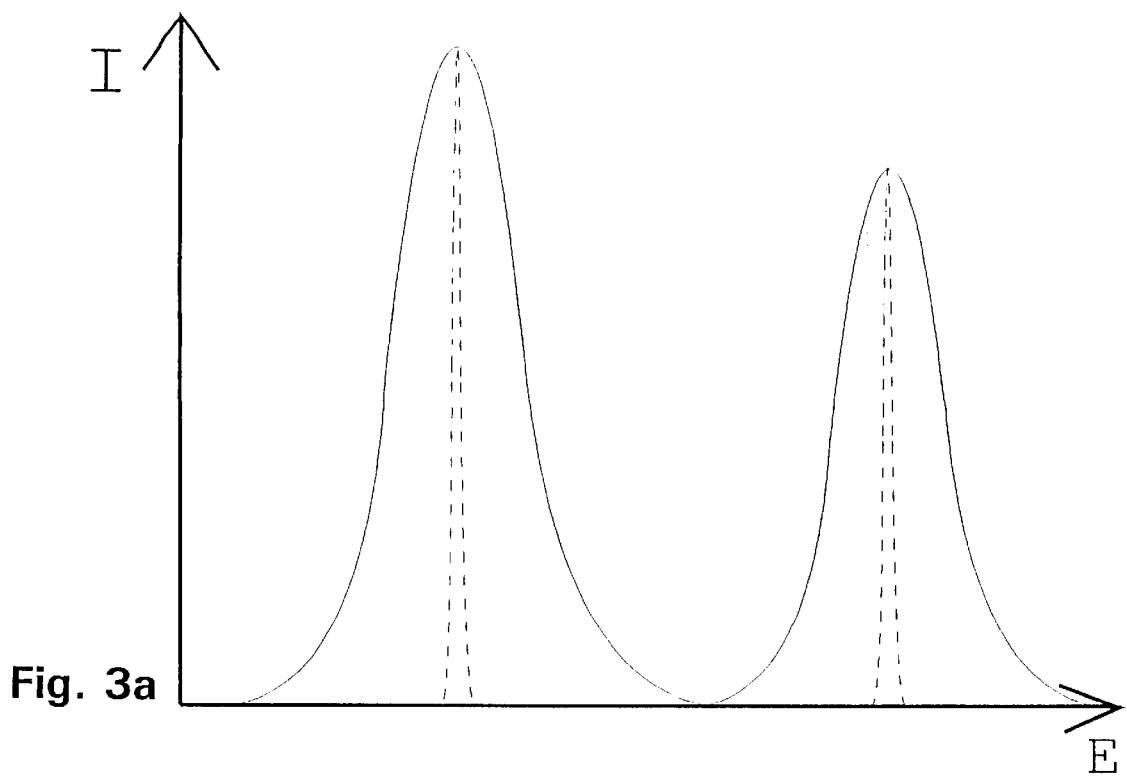
FIG. 3a and FIG. 3b show schematic diagrams of the energy or wavelength resolution of detector and wavelength selectors, wherein in FIG. 3a two wavelength selectors are associated with one detector.
Figure 3B:
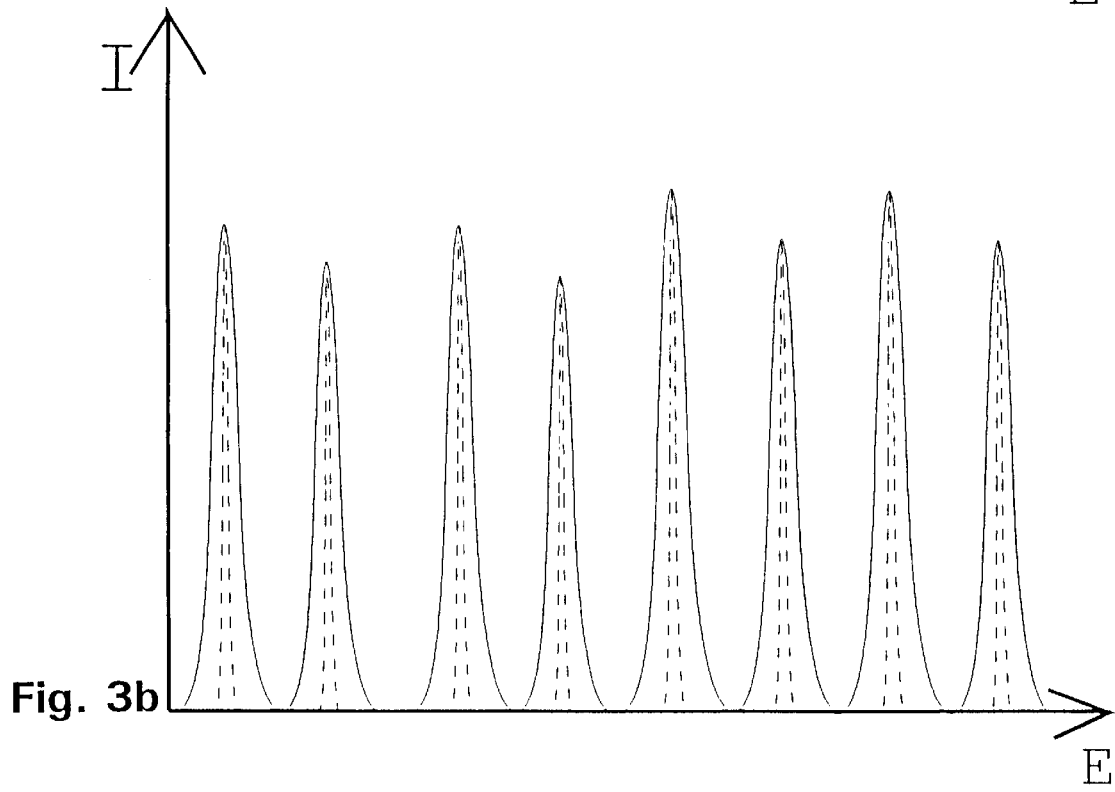

FIGS. 3a and 3b show examples of the energy resolution in a spectral diagram (intensity I vs. energy E).

FIG. 3a shows the case in which merely two wavelength selectors are associated with the same detector (see spectrometer 1 in FIG. 1), whereas FIG. 3b schematically shows the case in which one single detector is associated with a total of eight wavelength selectors (see also FIG. 2). In order to achieve reasonable results, the resolution of the wavelength selectors (dotted curves in FIGS. 3a and 3b) is usually higher than the resolution of the associated detector (full lines in FIGS. 3a and 3b).

In the example shown in FIG. 3a the detector may show only a moderately good energy resolution in the range of $\Delta E \approx 1000\text{--}2000$ eV at $E \approx 6$ keV. If the wavelength selectors have been selected appropriately, even with poor energy resolution of the detector, the two lines to be separated may be spaced apart from one another at such an energy distance that they can still be entirely resolved in the spectrum.

In the case of FIG. 3b, however, a detector is required which has a considerably better energy resolution, e.g. $\Delta E < 200$ eV, preferably $\Delta E \leq 30$ eV at $E=5.9$ keV. This requires of course a considerably higher effort with respect to the detector, wherein, however, considerably fewer detectors are required for the same total number of different wavelength bands. After all, the detector of FIG. 3b serves four times as many wavelength selectors as the detector of FIG. 3a. With further improving developments of detectors available in the future it will be possible to construct very compact spectrometers using the basic inventive idea, by means of which it will nevertheless be possible to record a large variety of different lines in different wavelength ranges.

What is claimed:

1. A spectrometer for the measurement of spectral lines emitted from a sample, the spectrometer comprising:
   at least one first wavelength selector for selecting first light from the sample, said first light having a first wavelength;
   at least one second wavelength selector for selecting second light from the sample, said second light having a second wavelength; and
   at least one detector, wherein said first wavelength selector and said second wavelength selector simultaneously supply said first and said second light to a common detector, said common detector being energy dispersive and having an energy resolution which is sufficient to separate detected light of said first and said second wavelengths.

2. The spectrometer of claim 1, wherein the spectrometer is an X-ray fluorescence spectrometer and said first and said second light from the sample is X-ray fluorescence light.

3. The spectrometer of claim 1, wherein several detectors are provided.

4. The spectrometer of claim 2, wherein only one detector is provided and wherein said energy resolution $\Delta E < 200$ eV at $E = 5.9$ keV.

5. The spectrometer of claim 1, wherein a wavelength resolution of said first and said second wavelength selectors is higher than said energy resolution.

6. The spectrometer of claim 1, wherein said at least one first and second wavelength selectors are arranged essentially in a plane in the form of a star about an axis between the sample and said detector.

7. The spectrometer of claim 1, wherein at least one of said first and said second wavelength selectors comprises focusing optics having an entrance slit, an analyzer element and an exit slit.

8. The spectrometer of claim 7, wherein said analyzer element is a single crystal.

9. The spectrometer of claim 7, wherein said analyzer element is a multilayer structure.

10. The spectrometer of claim 7, wherein said analyzer element is curved.

11. The spectrometer of claim 7, wherein several wavelength selectors, which are associated with said common detector, have a common exit slit.

12. The spectrometer of the claim 7, wherein at least one wavelength selector comprises an absorbing element.

13. The spectrometer of claim 12, wherein said absorbing element is arranged such that intensities of transmitted light of all wavelength selectors associated with said common detector differ by at the most one order of magnitude.

14. The spectrometer of claim 1, wherein there are between 4 and 10 wavelength selectors.

15. The spectrometer of claim 1, wherein there are between 2 and 8 wavelength selectors associated with said common detector.

16. The spectrometer of claim 1, wherein said at least one detector is a semiconductor detector.

17. The spectrometer of claim 4, wherein $\Delta E \leq 30$ eV at $E=5.0$ keV.

18. An X-ray fluorescence spectrometer for the simultaneous measurement of several spectral X-ray fluorescence lines emitted from a sample, the spectrometer comprising several wavelength selectors each selectively supplying light of a certain wavelength from the sample to at least one detector, wherein at least two different wavelength selectors supply X-ray fluorescence light from the sample to the same detector associated to the at least two wavelength selectors, wherein the at least one detector is energy-dispersive and has a sufficiently large energy resolution in order to energy-separate the detected X-ray fluorescence light of the various wavelengths from the at least two different associated wavelength selectors, wherein at least one wavelength selector comprises an absorbing element such that the X-ray fluorescence intensities transmitted by all wavelength selectors associated with the same detector differ by at most one order of magnitude, and wherein the resolution of the wavelength selectors is higher than the resolution of the associated detectors.

19. The spectrometer of claim 18, wherein only one detector is provided and wherein said energy resolution $\Delta E < 200$ eV at $E=5.9$ keV.

20. The spectrometer of claim 18, comprising only one detector.

21. The spectrometer of claim 20, wherein the wavelength selectors are arranged essentially in a plane in the form of a star about an axis between the sample and the detector.

22. The spectrometer of claim 19, wherein said energy resolution $\Delta E \leq 30$ eV at $E=5.9$ keV.

* * * * *